(12) United States Patent
Sabaria

(10) Patent No.: US 7,964,136 B2
(45) Date of Patent: Jun. 21, 2011

(54) METHOD OF STERILIZING POLYMERIC STRUTS AND STENTS

(75) Inventor: Patrick Sabaria, Saint Nom la Breteche (FR)

(73) Assignee: Arterial Remodeling Technologies, S.A., Noisy le Roi (FR)

( * ) Notice: Subject to any disclaimer, the term of this patent is extended or adjusted under 35 U.S.C. 154(b) by 275 days.

(21) Appl. No.: 12/282,680

(22) PCT Filed: Mar. 13, 2007

(86) PCT No.: PCT/IB2007/000587
§ 371 (c)(1),
(2), (4) Date: Sep. 12, 2008

(87) PCT Pub. No.: WO2007/125391
PCT Pub. Date: Nov. 8, 2007

(65) Prior Publication Data
US 2009/0074610 A1  Mar. 19, 2009

Related U.S. Application Data

(60) Provisional application No. 60/781,748, filed on Mar. 14, 2006, provisional application No. 60/781,747, filed on Mar. 14, 2006, provisional application No. 60/781,741, filed on Mar. 14, 2006, provisional application No. 60/791,220, filed on Apr. 12, 2006, provisional application No. 60/814,533, filed on Jun. 19, 2006, provisional application No. 60/854,075, filed on Oct. 25, 2006.

(51) Int. Cl.
| | |
|---|---|
| A61L 2/00 | (2006.01) |
| B01J 19/08 | (2006.01) |
| G01N 23/00 | (2006.01) |
| H01J 27/00 | (2006.01) |
| A61N 5/00 | (2006.01) |
| A61M 31/00 | (2006.01) |
| A61F 2/06 | (2006.01) |
| B65D 81/24 | (2006.01) |
| B65D 73/00 | (2006.01) |
| A61B 17/06 | (2006.01) |

(52) U.S. Cl. ..... 422/22; 422/1; 422/186.05; 250/455.11; 250/427; 250/492.1; 250/492.3; 604/48; 604/507; 604/508; 623/1.1; 623/1.5; 206/438; 206/484; 206/210

(58) Field of Classification Search ................ 422/1, 22, 422/186.05; 250/455.11, 427, 492.1, 492.3; 604/48, 507, 508; 623/1.1, 1.5; 206/438, 206/484, 210
See application file for complete search history.

(56) References Cited

U.S. PATENT DOCUMENTS

| | | | |
|---|---|---|---|
| 4,135,622 A * | 1/1979 | Glick | 206/63.3 |
| 4,279,249 A | 7/1981 | Vert et al. | |
| 5,527,337 A | 6/1996 | Stack et al. | |
| 5,769,883 A | 6/1998 | Buscemi et al. | |
| 5,957,975 A | 9/1999 | Lafont et al. | |
| 7,780,721 B2 * | 8/2010 | Bales et al. | 623/1.22 |
| 2005/0069452 A1 * | 3/2005 | Varma et al. | 422/22 |
| 2005/0233062 A1 * | 10/2005 | Hossainy et al. | 427/2.1 |
| 2006/0058863 A1 | 3/2006 | LaFont et al. | |
| 2008/0028594 A1 | 2/2008 | Lafont et al. | |

FOREIGN PATENT DOCUMENTS

| | | | |
|---|---|---|---|
| EP | 0 832 655 A2 * | 4/1998 | |
| EP | 1 389 471 A1 | 2/2004 | |

* cited by examiner

Primary Examiner — Jill Warden
Assistant Examiner — Monzer R Chorbaji
(74) Attorney, Agent, or Firm — Tarolli, Sundheim, Covell & Tummino LLP

(57) ABSTRACT

It has been determined that gamma sterilization of biodegradable polymer stents does not cause significant polymer crosslinking and collapse. Using sufficient spacing can lead to stents that display little if any detrimental effects from the procedure. In certain embodiments, using structures in the general region of about 100 micron spacing between the struts leads to highly functional stents that do not fuse. Further, the resulting stent has radially homogenous mechanical properties. Therefore, the stent has a uniform expansion within the lumen.

16 Claims, No Drawings

METHOD OF STERILIZING POLYMERIC STRUTS AND STENTS

RELATED APPLICATIONS

This application claims priority from PCT International Application No. PCT/IB2007/000587, which was filed on Mar. 13, 2007, and claims priority from U.S. Provisional Patent Application Nos. 60/781,748, filed Mar. 14, 2006, 60/781,747, filed Mar. 14, 2006, 60/781,741, filed Mar. 14, 2006, 60/791,220, filed Apr. 12, 2006, 60/814,533, 60/814,533, filed Jun. 19, 2006, and 60/854,075, filed Oct. 25, 2006 (all expired). The subject matter of the aforementioned applications is hereby incorporated by reference in their entireties.

BACKGROUND OF THE INVENTION

The use of stent medical devices to keep a duct, vessel or other body lumen open in the human body has developed into a primary therapy for lumen stenosis or obstruction. The use of stents in various surgical, interventional cardiology, and radiology procedures has quickly become accepted as experience with stent devices accumulates and as the advantages of stents become more widely recognized. Stents are often used in body lumens to maintain open passageways such as the prostatic urethra, the esophagus, the biliary tract, intestines, and various coronary arteries and veins, as well as more remote cardiovascular vessels such as the femoral artery.

Stents are often used to treat atherosclerosis, a disease in which vascular lesions or plaques consisting of cholesterol crystals, necrotic cells, lipid pools, excess fiber elements and calcium deposits accumulate in the walls of an individual's arteries. One of the most successful procedures for treating atherosclerosis is to insert a deflated balloon within the lumen, adjacent the site of the plaque or atherosclerotic lesion. The balloon is then inflated to put pressure on and "crack" the plaque. This procedure increases the cross-sectional area of the lumen of the artery. Unfortunately, the pressure exerted also traumatizes the artery, and in 30-40% of the cases, the vessel either gradually renarrows or recloses at the locus of the original stenotic lesion. This renarrowing is known as restenosis A common approach to prevent restenosis is to deploy a stent to the site of the stenotic lesion. Stents can be made from various conventional, biocompatible metals; however, several disadvantages may be associated with the use of metal stents. For instance, although metallic stents have the mechanical strength necessary to prevent the retractile or recoil form of restenosis, their presence in the artery can lead to biological problems including vasospasm, compliance mismatch, and even occlusion. Moreover, there are inherent, significant risks from having a metal stent permanently implanted in the artery, including erosion of the vessel wall. The stents may also migrate on occasion from their initial insertion location. Such stents cause irritation to the surrounding tissues in a lumen. Also, since metals are typically much harder and stiffer than the surrounding tissues in a lumen, this may result in an anatomical or physiological compliance mismatch, thereby damaging tissue or eliciting unwanted biologic responses. In addition, the constant exposure of the stent to the blood can lead to thrombus formation within the blood vessel. Stents also allow the cellular proliferation of the injured arterial wall to migrate through the stent mesh, where the cells continue to proliferate and eventually lead to the narrowing of the vessel. Further, metal stents typically have some degree of negative recoil. Finally, metallic stents actually prevent or inhibit the natural vascular remodeling that can occur in the organism by rigidly tethering the vessel to a fixed, maximum diameter.

Similar complications and problems, as in the case of metal stents, may well result when using stents made from non-absorbable biocompatible polymer or polymer-composites, although these materials may offer certain benefits such as reduction in stiffness.

Bioabsorbable and biodegradable materials for manufacturing temporary stents present a number of advantages. The conventional bioabsorbable or bioresorbable materials of the stents are selected to absorb or degrade over time to allow for subsequent interventional procedures such as restenting of the original site if there is restenosis and insertion of a vascular graft. Further, bioabsorbable and biodegradable stents allow for vascular remodeling, which is not possible with metal stents that tethers the arterial wall to a fixed geometry. In addition to the advantages of not having to surgically remove such stents, bioabsorbable and biodegradable materials tend to have excellent biocompatibility characteristics, especially in comparison to most conventionally used biocompatible metals. Another advantage of bioabsorbable and biodegradable stents is that the mechanical properties can be designed to substantially eliminate or reduce the stiffness and hardness that is often associated with metal stents, which can contribute to the propensity of a stent to damage a vessel or lumen. Examples of novel biodegradable stents include those found in U.S. Pat. No. 5,957,975, and U.S. application Ser. No. 10/508,739, which is herein incorporated by reference in its entirety.

It is often difficult to sterilize the biodegradable polymers of the stent, however, without causing damage to the polymer itself. For instance, it is difficult to use acid to sterilize because acid can very quickly degrade the polymer and hence affect its mechanical properties. Further, it is difficult to use autoclaving to steam sterilize a biodegradable polymer. In autoclaving, sterilization condition of high-pressure vapor is applied for about 20 minutes at 121° C. of 1.0 kg/cm$^2$G of saturated vapor pressure. While such conditions are possible in sterilization of many kinds of medical materials that stand high pressure and temperature, such sterilization methods are often problematic for organic polymer materials because of deterioration or decomposition of the material.

Many sterilizable devices that incorporate biodegradable polymers are sterilized by irradiating the device; however, there are also many problems with radiation. For instance, E-beam irradiation, particularly at doses above two Mrd, can induce significant degradation of the polymer chain, resulting in reduced molecular weight and altering the final mechanical properties and degradation time.

In addition, irradiation can cause cross-linking and collapsing of the polymer chains. Polymer cross-linking occurs because radicals are generated by the irradiation process, thereby generating new inter- and intramolecular connections of the polymer molecules. Further, the free radicals generated by irradiation do not immediately disappear, but remain in the polymer material and can cut polymer chains and lead to other problems by reacting with oxygen over time. The free radicals can generally be removed by heating the polymer to a temperature higher than 100° C.; however, this again would deform the polymer and alter its mechanical properties.

There are also differences between sterilizing metal and polymer stents by irradiation. For metal stents, the struts may be close together and even overlap during sterilization. Sterilization of biodegradable polymers by irradiation; however, may result in the struts fusing together. Further, radiation exposure may cause the polymer materials to cross-link or cause collapse of the polymer chains.

Therefore, EtO sterilization is commonly used for biodegradable polymers such as polyglycolide, poly (lactide), and poly (dioxanone). Because the highly toxic EtO can present a safety hazard; however, great care must be taken to ensure that all the gas is removed from the device before final packaging. Further, EtO sterilization occurs at elevated temperatures, and thus may again result in strut fusion.

In the case of biodegradable stents, the inventors have discovered that the stents can be sterilized by gamma irradiation when the space between the struts is large enough to prevent overlap and fusion of the struts. The inventors made the surprising discovery that carefully controlling the spacing between the struts yields superior results. This method yields stents with unexpectedly improved quality because there is minimal crosslinking and collapsing, resulting in struts that do not stick together.

SUMMARY OF THE INVENTION

The inventors have made the surprising discovery that gamma sterilization of biodegradable polymer stents does not cause significant polymer cross-linking and collapse. Using sufficient spacing can lead to stents that display little if any detrimental effects from the procedure. In certain embodiments, using structures in the general region of about 100 micron spacing between the struts leads to highly functional stents. This superior and unexpected result yields stents with improved qualities because the struts do not stick together. Further, the inventors have found that by preventing the struts from fusing, the resulting stent has radially homogenous mechanical properties. Therefore, the stent has a uniform expansion within the lumen. This uniform expansion is especially important when the stent is used in areas of the body where there is high stress or strain.

The present invention provides methods of gamma radiation to sterilize the biodegradable polymer stents while decreasing risk of polymer fusion and overlap. Further, the radiation sterilization may be applicable to biodegradable materials used in other devices.

DETAILED DESCRIPTION OF THE PREFERRED EMBODIMENT

The inventors have made the surprising discovery that gamma sterilization of biodegradable polymer stent does not cause polymer fusion if there is sufficient spacing between the struts. In certain embodiments, spacing in the range of 100 microns provides stents with highly functional qualities. This superior and unexpected result yields stents with unexpectedly improved qualities because the struts do not fuse or stick together.

While not wanting to be held to any particular theory, the inventors believe that the use of gamma sterilization with the proper spacing between struts results in preventing the polymer from decomposing and forming cross-linking between the polymer chains. If there is sufficient space between the struts, then there is minimal molecular reorganization and fusion of the struts. This prevents the deterioration of the stent mechanical properties caused by typical means of sterilization.

The details of the present invention are below.

I. Stent Fabrication and Properties

The stents may be formed from any biodegradable, biocompatible, bioresorbable polymer, preferably a thermoplastic polymer. As used herein, a bioresorbable polymer is one whose degradative products are metabolized in vivo or excreted from the body via natural pathways. The polymer of the stent can be a homopolymer or a copolymer. Preferably, the stent is formed from a thin layer of one or more amorphous, bioresorbable polymers, i.e., the polymers used to form the stent preferably are not crystalline. It is also preferred that the polymers used to form the stent do not generate crystalline residues upon degradation in vivo. It is also contemplated that the chains of the polymer may be or may not be cross-linked. Light cross-linking is acceptable, however, if thermal and viscoelastic characteristics that allow education, crimping, and deployment of the device are sufficiently maintained.

Appropriate biodegradable polymers may include, but are not limited to, poly(L-lactide), polyglycolide, poly(D,L-lactide), copolymers of lactide and glycolide, polycaprolactone, polyhydroxyvalerate, polyhydroxybutyrate, polytrimethylenecarbonate, polyorthoesters, polyanhydrides, and polyphosphazenes. Examples of the types of polymers that are suitable for the stent of the present invention include, but are not limited to, lactic acid-based stereocopolymers (PLAx copolymers composed of L and D units, where X is the percentage of L-lactyl units) (55<Tg<60), copolymers of lactic and glycolic acids (PLAxGAy, where X, the percentage of L-lactyl units, and Y, the percentage of glycolyl units, are such that the Tg of the copolymer is above 45° C.), and Poly(lactic-co-glycolic-co-gluconic acid) where the OH groups of the gluconyl units can be more or less substituted (pLAxGayGLx, where X, the percentage of L-lactyl units, and Y, the percentage of glycolyl units, and Z the percentage of gluconyl units are such that the Tg of the terpolymer is above 45° C.). Other suitable polymers include, but are not limited to, polylactic acid (PLA), polyglycolic acid (PGA) polyglactin (PLAGA copolymer), polyglyconate (copolymer of trimethylene carbonate and glycolide, and a copolymer of polyglycolide or lactide acid or polylactic acid with .epsilon.-caprolactone), provided that the polymer has a glass transition temperature, Tg, of at least 45° C. or greater.

In one preferred embodiment, the stent comprises a polylactic acid stereocopolymer produced from L and DL lactides. The polymer is designated herein as "PLAX" where X represents the percentage of the L-lactic acid units in the mixture of monomers used to prepare the lactides. Preferably X is in the range of 10 to 90, more preferably 25 to 75. In another preferred embodiment, the stent comprises a polylactic acid, glycolic acid copolymer produced from L and DL lactides and glycolides. The polymer is designated herein as "PLAXGAY" where Y represents the percentage of glycolic acid units in the mixture of monomers used to prepare the copolymers. Preferably, the copolymers do not contain glycolyl repeating units since such units are known to be more inflammatory than lactyl repeating units. Preferably, the polymers are prepared using Zn metal or Zn lactate as initiator. To ensure good initial mechanical properties of the stent, the molecular weight of the polymer in the region having the second in vivo lifetime is preferably above 20,000 daltons, most preferably 100,000 daltons or greater. The polydispersity, I=Mw/Mn, should preferably be below two and should not greatly reflect the presence of low molecular weight oligomers smaller than 2,000 daltons as determined by size exclusion chromatography. Optionally, the polymeric layer used to make the stent may be impregnated with an anticoagulant agent, such as heparin, anti-oxidants, such as vitamin E, compounds that regulate cellular proliferation, or anti-inflammatory drugs, such as corticosteroids, to provide localized drug delivery. Such drugs are incorporated into the polymeric layer using techniques known in the art. Agents may also be incorporated into the base polymer that forms the body of the stent, as long as the incorporation does not have significant adverse effects on stent desired physical characteristics such as radial stent deployment and degradation time. For intravascular stents, it is preferred that the film have a thickness of from about 0.05 mm to 0.2 mm.

It is contemplated that the stent may be made by any method. In one preferred embodiment, the stent is a formed from a biodegradable polymeric band comprising a head having a slot and a tongue comprising a catch or locking mechanism proximate the longitudinal edge thereof. The cylindrical element, which has an inner and outer surface, is formed by inserting a portion of the tongue through the slot to provide a cylindrical element having a first reduced diameter configuration. Following deployment, the cylindrical element is in a second expanded diameter configuration wherein the distal catch mechanism engages the inner surface of the head and prevents radial collapse or recoil of the polymeric stent. In a second preferred embodiment, the stent is formed from a plurality of interconnected polymeric bands each of which comprises a head having a slot and a tongue comprising a catch mechanism proximate the longitudinal edge thereof.

In one embodiment, the stent is formed by laser cutting a flat polymeric sheet in the form of the stent, and then rolling the pattern into the shape of the cylindrical stent and providing a longitudinal weld to form the stent. In yet another embodiment the stent is created from a hollow cylinder into which a pattern is cut with a laser. In another embodiment, the stents are created by chemically etching a flat polymeric sheet and then rolling and welding it to form the stent, or coiling a polymeric wire to form the stent.

In another preferred embodiment, the stent may also be formed by molding or injection molding of a thermoplastic or reaction injection molding of a thermoset polymeric material. The flat grid is then rolled and extremities are welded or glued to form a cylinder. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

Generally, the struts are arranged in patterns that are designed to contact the lumen walls of a vessel and to maintain integrity of the vessel thereby. A myriad of strut patterns are known in the art for achieving particular design goals.

The space between the stent struts can have virtually any configuration as long as the struts do not fuse and result in overlap during gamma radiation. It is contemplated that the space between the struts be at least about 25 microns to 5000 microns more preferably 50 to 2000 microns and most preferably 90 to 500 microns. In a most preferred embodiment, the space between the struts is at least about 100 microns.

Typically, stents are composed of an intricate geometric pattern of circumferential and longitudinally extending members. The stent may also be a polymeric cylindrical device that incorporates slits or open spaces to allow for a reduction in diameter of the cylindrical tube without substantially altering the wall thickness.

It is contemplated that a crimped stent may incorporate slits or open spaces to allow for the temporary reduction in diameter of the cylindrical tube without substantially altering the wall thickness. Moreover, a stent embodying the present invention can include teeth and corresponding catching structure that operates to maintain an expanded form. Moreover, polymer based stents embodying structure defined by a wire or ribbon coil or helix or a knitted mesh configuration are possible examples of self-expanding stents which also may benefit from the present invention. Other important design characteristics of stents include radial or hoop strength, expansion ratio or coverage area, and longitudinal flexibility. One strut pattern may be selected over another in an effort to optimize those parameters that are of importance for a particular application.

It is also contemplated that the biodegradable stent may also have a programmed pattern of in vivo degradation. Stent polymeric structure allows for differential speed degradation. See, for example, U.S. Pat. No. 5,957,975, the entirety of which is incorporated by reference. In one embodiment, the stent comprises at least one substantially cylindrical element having two open ends and a plurality of regions circumferentially spaced around the cylindrical element and extending from one open end to the other open end of the cylindrical element. Each of the regions is configured or designed to have a desired in vivo lifetime. At least one of the regions is designed to have a shorter in vivo lifetime than the other region or regions. This means that the region having the shorter in vivo lifetime degrades sooner after deployment than the regions having a longer in vivo lifetime. Thus, when stents designed in accordance with the present invention are deployed within the lumen of a vessel of a patient, the cylindrical element acquires one or more fissures which extend from one open end of the cylindrical element to the other open end of the cylindrical element within a desired, predetermined period of time after the stent is deployed in the patient. It has been determined that such fragmentation within a predetermined period of time after deployment allows for enlargement of the lumen of the vessel via the process of arterial remodeling.

The regions of the stent with the different in vivo lifetimes can be made in a variety of ways. Preferably, such stents are made by producing regions having a first in vivo lifetime, i.e. a shorter in vivo lifetime, in a polymeric layer having the predetermined second, or longer, in vivo life time. The regions having the first in vivo lifetime are produced by heating the respective regions of the polymeric layer having a second in vivo lifetime for a time and at a temperature sufficient to cause local partial degradation of the polymeric chains. Such treatment, which can be accomplished using a piloted hot needle, laser beam, or flow of hot air, renders the polymer in the heated region more sensitive to hydrolytic degradation. Alternatively, the regions having a first in vivo lifetime may be produced in a polymeric layer having a second in vivo lifetime by incorporating a sufficient number of acidic ions into the respective regions of the polymeric layer. Preferably, the acidic ions are provided by compounds that are not soluble in blood.

Regions having a first in vivo lifetime can also be produced in a polymeric film having a second in vivo lifetime by exposure of the respective regions to beta radiation or gamma radiation for a sufficient time to induce partial cleavage of the polymeric chains within the respective regions. Provided the polymeric layer has a thickness of less than 0.3 mm, regions having a first in vivo lifetime can also be produced in a polymeric film having a second in vivo lifetime by introducing areas of mechanical weakness into the polymer. One method of introducing mechanical weakness is by reducing the thickness of the polymer in the respective region or forming holes therein. Regions having a first in vivo lifetime can also be produced in a polymeric film having a second in vivo lifetime by applying mechanical stress to the respective region. However, this latter process is difficult to control and, thus, is less preferred. Differing lifetimes can also be created by providing one or more different coatings over different regions of the biodegradable stent.

Another method for producing a polymeric layer in which one region or a plurality of spaced apart regions have a first in vivo lifetime and other regions have a second in vivo lifetime is to incorporate strips or fibers of a faster degrading bioresorbable polymer into a film made from a slower degrading polymer. For example, a mesh or a parallel array of fibers or strips of PGA or any other faster degrading bioresorbable polymer can be embedded into the respective regions of a polymeric film of PLA that may be designed to be slower degrading. Embedding can be achieved by inserting the mesh or fibers between two melted sheets of the slower degrading polymer. Provided the relative solubilities are compatible, the fibers or mesh can be placed in an organic solution of the slower degrading polymer and the desired polymeric film formed by evaporation of the organic solvent. One example of a method for embedding a mesh made from one polymer into a polymeric layer made from a second polymer is described in U.S. Pat. No. 4,279,249 issued to Vert et al. on Jul. 21, 1981, which is specifically incorporated herein by reference. A stent having the desired shape and orientation of regions is then formed from the polymeric layer by standard techniques such as stamping, employing a laser beam, or any other technique used in the art to tool a polymeric film.

It is further contemplated that the stent include additional additives that may add onto the polymer or blended with the polymer before stent formation. The additives may be distributed uniformly throughout the stent or confined to selected regions. These additives may be released from the stent quickly or slowly over time. The mechanism by which the additives are released is not limited. The additives contemplated is not limited in any way and may include anti-inflammatory agents, drugs, vascular growth factors, and anti-clotting agents, heat stabilizers, antioxidants, ultraviolet absorbance, light stabilizer, colorant, lubricant, nucleating agent, fired retardant, or filler. Furthermore, it is possible to blend the polymer with known heat stabilizer, antioxidant, ultraviolet absorbent, light stabilizer, colorant, antistatic, lubricant, nucleating agent, fire retardant, or filler within limit of not spoiling the effect of the present invention.

Furthermore, various methods are contemplated for addition of the additives to a polymer material. For example, the additives can be dip coated on a polymeric structure of a stent or other device. Moreover, the additives alone or blended with other materials can be added to the surface of a device by way of a plasma spray or etch or by employing thermal pressure or heat and pressure. Steriolithography and blow molding are other contemplated approaches. In addition, the additives can be mixed with a biocompatible epoxy resin, whereby the additives are blended with another material and coated to the inner diameters, outer diameter or sides of structures defining the stent. It is contemplated that the additives may be added to the stent at anytime, including before or after the gamma sterilization.

The length, diameter, and strut thickness of the stent can be of any size. However, it is contemplated that these parameters will be limited by the performance features desired. Further, the stent may be used for any tubular body structure, including but not limited to, coronary, neurological, carotid, renal, iliac, biliary, aortic, femoral, or other peripheral indication.

While it is at the final predetermined shape, size, and diameter, the cylindrical device is educated by heating the device to a temperature above the Tg of the polymer from which the device is formed. The device is heated for a time sufficient to erase any former process-related memory and to impart a new memory of the final predetermined shape and diameter to the polymeric cylindrical device. It is believed that such conditions allow the polymer chains to relax and reorganize themselves from an entanglement typical of the former processing stages to an entanglement typical of the high temperature at which the cylindrical device is compatible with the final or deformed shape and size. When the polymeric cylindrical device has an initial diameter that is less than the final predetermined diameter, it is desired to heat to a temperature well above the Tg of the polymer. This heating step erases the anisotropic stresses promoted by the extrusion or molding process and the former processing-related memory of the polymer chains. Good results have been obtained by heating a laser-precut or molded polymeric cylindrical device formed from PLA75 or other PLAs and deformed from a diameter of 1 mm to 4 mm at a temperature of 80° C. for 30 minutes. Temperatures of from about 45° C. to about 120° C. and times of 5 minutes or more should be suitable for educating stents made from PLAx with $0<X<100$, PLAxGAy with $0<X<25$ and $75<Y<100$, or any PLAxGAyGLz.

The polymeric cylindrical device is then crimped. "Crimping" as used herein refers to a process that involves radial pressing on a polymeric cylindrical device having slits, or openings in the wall thereof to allow a decrease in the diameter of the device without substantially affecting the thickness of the wall or struts of the cylindrical device. Such process may also result in an increase in length of the cylindrical device.

To crimp the educated cylindrical device, it is mounted onto a device with a smaller diameter. The diameter of the educated cylinder is reduced by heating the cylinder to a temperature below the Tg of the polymer while evenly applying pressure on the exterior surface of the wall of the cylindrical device. Examples of crimping may be found in U.S. application Ser. No. 10/541,421 and U.S. application Ser. No. 10/508,739, which is herein incorporated by reference in its entirety.

In some embodiments, the polymeric stent is crimped onto an inflatable device such as an inflatable balloon catheter. In this instance, the stent assembly after crimping comprises an inflatable balloon catheter and an expandable, educated, polymeric stent snugly and stably disposed thereon. The temperature at which the cylindrical device is heated during crimping is high enough to allow reduction in diameter of the cylindrical device but low enough to not erase the memory of the final predetermined shape and diameter of the educated cylindrical device. Ideally, the temperature is less than the glass transition state of the polymer. More preferably, the temperature is at about 50° C. Thus, the temperature at which the educated cylindrical device is heated during crimping is less than the temperature at which the cylindrical device is heated during education of the cylindrical device. Further, the time it takes to crimp the educated cylindrical device can vary, depending upon the temperature, size and composition of the stent In accordance with the present method, expansion of the polymeric stent can be achieved by any means. In one embodiment, a balloon is used merely as a carrier for the stent through the body. In this preferred embodiment, the stent expansion occurs by the positive recoil properties of the stent; thus, the expansion is balloon inflation independent. In another preferred embodiment, a balloon is inflated and/or heated to initiates the stent expansion. It is contemplated that the positive recoil properties of the stent will expand the stent to its final predetermined diameter. The temperature used to initiate the stent expansion may be any temperature at or below the Tg of the polymer. In a less preferred embodiment, a balloon is inflated to expand the polymeric stent to its final predetermined shape.

In another aspect, the method of the present invention starts with a polymeric tube whose diameter initially is less than the final predetermined diameter. Such tube is first heated to a temperature close to or above the Tg of the polymer and expanded to provide a cylindrical device whose diameter is equal to the final desired diameter. Thereafter the cylindrical device is educated as described above to provide an educated cylindrical device having a memory of the final predetermined shape and diameter, and then crimped on a balloon catheter as described above to provide an assembly comprising the balloon catheter and an expandable, educated, polymeric stent snugly and stably disposed thereon.

The present invention also provides an assembly comprising an inflatable balloon catheter and a polymeric stent prepared in accordance with the present method.

Advantageously, the stent of the present invention exhibits little to no relaxation-related negative recoil when deployed in the blood vessel of a subject. Advantageously, the assembly of the present invention has a diameter that allows it to be easily inserted into a blood vessel of the subject and advanced to a target site. Advantageously, the stent of the present invention exhibits expansion (positive recoil) and adaptation to the geometry of the artery when the stent is not fully deployed up to its final diameter during deployment. Positive recoil over several days will create outward radial pressure for long periods of time. This outward radial pressure aids in positive vascular remodeling by assisting stabilizing the injured artery, assisting in cellular progress to repair injury of original acute expansion, assisting in security of tissue flaps, and the like.

In addition, the stent of the present invention is stably disposed on the balloon, meaning that a mechanical restraint is not required to prevent the stent from rapidly expanding to its final diameter during storage at room temperature. Thus, although not required, the assembly of the present invention, optionally, also comprises a retractable sheath covering the exterior surface of the stent. Such sheath serves to prevent deformation of the stent and preclude or slow expansion during storage.

Temperatures and times suitable for educating the cylindrical device and for thereby developing a stent resistant to negative recoil can be assessed by first crimping the stent of the present invention onto a balloon catheter. The balloon is then inflated to initiate stent expansion. The balloon is removed and the stent is stored at 37° C. While in storage, the stent may increase in diameter because of the positive recoil properties of the stent. If the stent exhibits little to no negative recoil when stored under these conditions for 4 to 6 weeks or, preferably the time estimated for an artery wall to recover from PTC angioplasty, the times and temperatures employed for educating the stent are suitable. In those cases where the polymeric stent exhibits a small amount of recoil, the cylindrical device can be educated at a diameter slightly larger than the final predetermined diameter to compensate for the small amount of negative recoil.

Temperatures and times suitable for crimping the stent to a reduced diameter can be assessed by allowing the stent-mounted balloon catheter of the present assembly to stay at room temperature or at the storage temperature. If the crimped stent stays collapsed at the small diameter corresponding to the deflated balloon under these conditions, the times and temperatures employed during crimping are suitable.

Optimization of stent mechanical properties such as positive recoil can be achieved by storing the finished product at a room temperature below 20° C. Preferably, the finish product is refrigerated at about 6° to 8° C.

II. Stent Packaging and Sterilization

The stent may be packaged by any means. For instance, the stent may be packaged by itself or it may be mounted onto a balloon catheter before packaging. Moreover, it is contemplated that the stent packaging device be fabricated from any suitable material that can be conventionally formed and processed, including but not limited to, polypropylene, polyethylene, a nylon/polyethylene blend, or polytetrafluoroethylene (PTFE). It is desirous to have packaging materials that minimize exchange of chemical components between the stent and the packaging during shipment and storage. That is, such materials may be nonreactive with a therapeutic agent carried in a stent coating or with other desirable coating materials. This would reduce or eliminate the risk of a therapeutic agent or other coating component migrating out of the coating and into the device material. Further, this would help prevent components of the device material from migrating into the therapeutic agent or other coating material. Further, it is important that the packaging is compatible with the sterilization process and can maintain the sterility under storage conditions.

The gamma sterilization methods may be by any means that can be performed by one skilled in the art. It is contemplated that any conventional gamma ray producing device may be used in the practice of the invention. Further, the doses must be sufficient to produce the FDA required sterility assurance level of $10^{-6}$ for the devices described herein. The dosage is required for obtaining the sterility assurance level for the device however can be determined from "Association for the Advancement of Medical Instrumentation Guidelines" published in 1992, the disclosure which is incorporated herein by reference. Preferably, the polymer stent is sterilized by gamma radiation at about 2.0-4.0 Mrad. Most preferably, the polymer stent is sterilized at about 2.5 Mrad.

Standard gamma sterilization procedures are suitable for obtaining sterility; however, gamma sterilization performed under specific conditions could further improve the preservation of polymer molecular mass. For instance, the stent should be sterilized under conditions that do not lead to reactions with the environment, e.g., in an inert gas environment. Further, it is desirable to control the humidity and other parameters during the sterilization.

It is also contemplated that the stent assembly be sterilized more than one time. For instance, the stent may be sterilized before or after the stent is sealed in its package. Moreover, the balloon catheter may be sterilized more than once. For example, the balloon may be sterilized by itself and then the balloon-stent assembly be sterilized once the stent is mounted onto the balloon. In addition, the sterilization can occur during its manufacture, i.e., as an integral in-line step in the manufacturing process, or alternatively, once the stent is fabricated.

In addition, use of gamma radiation is known to decrease the molecular weight of polymers. Therefore, the parameters of the gamma sterilization may be such that the radiation is used to decrease the stent molecular weight to a desired value. The gamma radiation may also be used to decrease the in vivo lifetime of all or part of the stent.

III. Deployment of the Stent

The polymer-based stent is first preheating for a period of 3 to 6 min at around 37° C. The preheating of the stent can occur by any means, including heating in saline, the blood stream, or hot air. After the preheating period, the polymer-based stent assembly of the present invention is introduced into a duct, tube, or vessel, e.g., a blood vessel of a mammalian subject, preferably in conjunction with a guiding catheter, and advanced to a target site, e.g. the site of stenotic lesion. After it is located at the target site the balloon is rapidly inflated thereby causing expansion of the stent to its final desired diameter or slightly below its final diameter. Optionally, the inflation fluid, balloon and stent are heated to a temperature above body temperature to aid in expansion. During this process the diameter of the stent increases, but the thickness of the walls of the stent remain substantially the same. As an alternative, the stent may be placed on a deployment device that is capable of localized heating of the stent when the stent is correctly positioned.

It is further contemplated that fracturing of the plaque and deployment of the stent may be done concurrently. If a balloon is used in such cases, the balloon is inflated to a pressure of about 8 to 12 atmospheres to crack the plaque and expand the stent. Alternatively, the vessel may be pre-dilated using angioplasty without the stent. Thereafter, the stent is introduced into the desired site on a separate catheter, preferably an expanding balloon catheter.

It is to be recognized that aspects of the present invention are applicable to other medical devices. For example, the disclosed formulations can be employed to create a passive marker on an interventional or surgical device, such as a biopsy needle or other hand-held devices. In addition, entire medical devices or portions thereof can embody the imageable material of the present invention.

While only the presently preferred embodiments have been described in detail, as will be apparent to those skilled in the art, alternatives, additions, modifications and improvements maybe made to the device and method disclosed herein without departing from the scope of the invention. Accordingly, it is not intended that the invention be limited, except as by the appended claims.

Example 1

A film of PLA 92 is used to prepare a stent comprising a single substantially cylindrical element comprising regions with different in vivo lifetimes. PLA 92 is synthesized from a mixture of 84/16 L-lactide/DL-lactide (PLA 92). The monomer is introduced into a reactor with 0.05% of zinc powder as primer. The polymerization occurs at 145° C. under vacuum for 8 days. The resulting polymers are purified by dissolution and precipitation using acetone or chloroform as solvent and ethanol as nonsolvent. The size exclusion chromatography is done using a WATERS apparatus, equipped with two columns of styragel and refractometric detector, the mobile phase being dioxane. The DSC thermograms are taken using a Dupont calorimeter, Series 99, equipped with a cell, the temperature increase being 10° C./min.

The polymer is formed into a film of about 0.1 to 0.2 mm thickness by means of compression molding. Then a stent with a tongue-latch mechanism is made from the film by stamping with a metal punch. To have a stent of three different expanded diameter configurations, three pairs of opposing teeth are placed along the lateral edges of the tongue. The overall length is 15 mm, the height of the cylinder being 9 mm at the level of the tongue and 15 mm at the level of the head. The slot is 8.5 mm long, the teeth measured 0.1 mm from base to tip. The total length of the tongue is 13 mm, the length of the body 7 mm, the combined body and tongue measured 20 mm. The bulkiness is reduced by diminishing the thickness of the polymer film used to around 0.15 mm. The tongue is inserted into the slot and the stent is then placed in a water bath at temperature of 50° to 60° C. and rolled up into a cylinder having a first reduced diameter configuration. The rolling is done around a metal guide of 0.014 inches. A gold ribbon is then crimped onto one strut at each end of the stent body length such that the gold ribbon markers are 7 mm apart.

The guide is then introduced into the lumen of a balloon catheter and the stent is then slid from the guide and advanced over the deflated balloon. The entire assembly is placed in the bath at a temperature of between 50° to 60° C. and the stent is firmly secured to the balloon by tightly squeezing the cylinder around the balloon. The mechanical stresses applied to the stent during assembly can generate visually detectable defects in the stent. It is believed that such defects resulted in the formation in the stent of regions having a shorter in vivo lifetime. The assembly is then enclosed within its packaging and sterilized at 20 kGy. This assembly is now ready to insert into a person or animal.

In addition to coronary arteries, the present stent may be used in other arteries such as for example, femeroiliac arteries, the carotid artery, vertebro-basilar arteries, as well as in the interior of other hollow passageways such as for example veins, ureters, urethrae, bronchi, biliary and pancreatic duct systems, the gut, eye ducts, and spermatic and fallopian tubes.

It is to be recognized that aspects of the present invention are applicable to other medical devices. For example, the disclosed method of radiation can be used to sterilizing an interventional or surgical device, such as a biopsy needle or other hand-held devices.

While only the presently preferred embodiments have been described in detail, as will be apparent to those skilled in the art, alternatives, additions, modifications and improvements maybe made to the device and method disclosed herein without departing from the scope of the invention. Accordingly, it is not intended that the invention be limited, except as by the appended claims.

The invention claimed is:

1. A method of sterilizing a polymer device by use of gamma radiation, whereby said polymer device comprises struts and the distance between the struts is such that the struts do not fuse;
    whereby said sterilization is used to decrease the in vivo lifetime of all or part of a polymer used in said polymer device.

2. The method of claim 1, whereby the distance between said struts is at least 50 microns.

3. The method of claim 2, whereby the distance between said struts is between 100 microns and 400 microns.

4. The method of claim 1, whereby said polymer device comprising struts is a stent.

5. The method of claim 1, whereby the gamma radiation is between 2.0-4.0 Mrad.

6. The method of claim 5, whereby the gamma radiation is 2.5 Mrad.

7. The method of claim 1, whereby said polymer device is mounted onto a balloon catheter.

8. The method of claim 1, whereby said polymer device is sealed in packaging before sterilization.

9. The method of claim 8, whereby said packaging is composed of materials that minimize exchange of chemical components between said polymer device and the packaging.

10. The method of claim 8, whereby said polymer device is sealed in packaging such that the packaging maintains sterility under storage conditions.

11. The method of claim 1, whereby said polymer device further comprises a therapeutic agent.

12. The method of claim 1, whereby said sterilization occurs in the presence of an inert gas.

13. The method of claim 1, whereby the humidity is controlled during sterilization.

14. The method of claim 1, whereby said polymer device is sterilized more than one time.

15. The method of claim 1, whereby said sterilization is used to decrease the polymer molecular weight of said polymer device to a desired value.

16. A method of sterilizing a polymer device by use of gamma radiation, said method consisting of the steps of:
  providing a polymer device, whereby said polymer device comprises struts and the distance between the struts is such that the struts do not fuse; and
  applying said gamma radiation to said polymer device.

* * * * *